(12) United States Patent
Golding et al.

(10) Patent No.: US 10,688,125 B2
(45) Date of Patent: Jun. 23, 2020

(54) NANOPARTICLES AND THEIR USE IN CANCER THERAPY

(71) Applicant: Midatech Ltd, Abingdon Oxfordshire (GB)

(72) Inventors: Jon Golding, Milton Heynes (GB); Phillip Williams, Oxford (GB); Meike Roskamp, Didcot (GB)

(73) Assignee: Midatech Ltd., Abingdon, Oxfordshire (GB)

( * ) Notice: Subject to any disclaimer, the term of this patent is extended or adjusted under 35 U.S.C. 154(b) by 4 days.

(21) Appl. No.: 15/538,828

(22) PCT Filed: Dec. 22, 2015

(86) PCT No.: PCT/EP2015/081070
§ 371 (c)(1),
(2) Date: Jun. 22, 2017

(87) PCT Pub. No.: WO2016/102613
PCT Pub. Date: Jun. 30, 2016

(65) Prior Publication Data
US 2017/0340665 A1    Nov. 30, 2017

(30) Foreign Application Priority Data
Dec. 23, 2014    (GB) .................................. 1423049.4

(51) Int. Cl.
*A61K 33/24* (2019.01)
*A61K 47/54* (2017.01)
(Continued)

(52) U.S. Cl.
CPC ............ *A61K 33/24* (2013.01); *A61K 9/0014* (2013.01); *A61K 47/549* (2017.08);
(Continued)

(58) Field of Classification Search
CPC .. A61K 33/24; A61K 9/0014; A61K 47/6929; A61K 47/549; A61K 45/00
See application file for complete search history.

(56) References Cited

U.S. PATENT DOCUMENTS

2012/0301535 A1* 11/2012 Williams ......... A61K 47/48861
424/443

FOREIGN PATENT DOCUMENTS

WO         02/32404 A2    4/2002
WO    2004/108165 A2    12/2004
(Continued)

OTHER PUBLICATIONS

Lund et al. ("The influence of ligand organization on the rate of uptake of gold nanoparticles by colorectal cancer cells"; 2011; Biomaterials; 32:9776-9784 (Year: 2011).*
(Continued)

*Primary Examiner* — Timothy P Thomas
(74) *Attorney, Agent, or Firm* — Kathleen D. Rigaut; Howson & Howson LLP

(57) ABSTRACT

The present invention provides a nanoparticle comprising a core comprising a metal; and a corona comprising a plurality of ligands covalently linked to the core, the plurality of ligands including at least a first species of ligand comprising an ethylene glycol portion and an amine group and at least a second species of ligand comprising a carbohydrate group, for use in a method of treating a cancer, particularly skin cancer, in a mammalian subject. Also disclosed are methods of treatment by administering the nanoparticles alone or in combination with radiotherapy.

13 Claims, 12 Drawing Sheets

(51) Int. Cl.
A61K 47/69 (2017.01)
A61K 9/00 (2006.01)
A61N 5/10 (2006.01)

(52) U.S. Cl.
CPC ...... *A61K 47/6923* (2017.08); *A61K 47/6929* (2017.08); *A61N 5/10* (2013.01); *A61N 2005/1098* (2013.01)

(56) References Cited

FOREIGN PATENT DOCUMENTS

| WO | 2005/091704 | A2 | | 10/2005 | | |
|----|-------------|----|---|---------|---|---|
| WO | 2005/116226 | A2 | | 12/2005 | | |
| WO | 2006/037979 | A2 | | 4/2006 | | |
| WO | 2007/015105 | A2 | | 2/2007 | | |
| WO | 2007/122388 | A2 | | 11/2007 | | |
| WO | 2011/154711 | A1 | | 12/2011 | | |
| WO | 2012/170828 | A1 | | 12/2012 | | |
| WO | 2014/125256 | A1 | | 8/2014 | | |
| WO | WO-2016075211 | A1 | * | 5/2016 | ........... | A61K 9/0019 |

OTHER PUBLICATIONS

Skin Cancer Foundation ("Squamous Cell Carcinoma (SCC): The Second Most Common Form of Skin Cancer"; https://www.skincancer.org/skin-cancer-information/squamous-cell-carcinoma; Nov. 11, 2013; Internet archive capture (Year: 2013).*

Dreaden et al.; Size Matters: gold nanoparticles in targeted cancer drug delivery; 2012; Ther. Deliv; 3(4): 457-478 (Year: 2012).*

Lung, Torben et al., "The influence of ligand organization on the rate of uptake of gold nanoparticles by colorectal cancer cells", Biomaterials, 32: 9776-9784 (2011).

Ghosh, Partha et al., "Gold nanoparticles in delivery applications", Advanced Drug Delivery Reviews, 60: 1307-1315 (2008).

Geng, Feng et al., "Pegylated Glucose Gold Nanoparticles for Improved In-Vivo Bio-Distribution and Enhanced Radiotherapy on Cervical Cancer", Journal of Biomedical Nanotechnology, 10: 1205-1216 (2014).

Feng, G. et al., "Enhancing multimodality functional and molecular imaging using glucose-coated gold nanoparticles", Clinical Radiology, 69: 1105-1111 (2014).

Marradi, Marco et al., "Glyconanoparticles: Polyvalent Tools to Study Carbohydrate-Based Interactions", Advances in Carbohydrate Chemistry and Biochemistry, 64: 211-290 (2010).

Cui et al., "Neoplastic cell response to tiopronin-coated gold nanoparticles", Nanomedicine: Nanotechnology, Biology, and Medicine, 9: 264-273 (2013).

Schaeublin et al., "Surface charge of gold nanoparticles mediates mechanism of toxicity", Nanoscale, 3: 410-420.

Setua et al., "Cisplatin-tethered gold nanospheres for multimodal chemo-radiotherapy of glioblastoma", Nanoscale, 6 (18): 10865-10873 (2014).

International Search Report/Written Opinion issued in corresponding International Application No. PCT/EP2015/081070, filed Dec. 22, 2015.

* cited by examiner

NANOPARTICLES AND THEIR USE IN CANCER THERAPY

Cross-Reference to Related Applications

This application is a § 371 of International Application No. PCT/EP2015/081070, filed Dec. 22, 2015, which claims priority from Great Britain Patent Application No. 1423049.4, filed Dec. 23, 2014. The entire disclosure of each of the aforesaid applications is incorporated by reference in the present application.

FIELD OF THE INVENTION

The present invention relates to nanoparticles and use thereof in the treatment of cancer.

BACKGROUND TO THE INVENTION

The present invention is directed at compositions and products, and methods of making and administering such compositions and products, including for the treatment of mammals and particularly humans.

Cancer is currently the second leading cause of death in both the USA and Europe. Squamous-cell carcinoma (SCC) is typically treated using topical medication, surgical excision with a free margin of healthy tissue and/or radiotherapy.

WO2011/154711 describes glycated gold nanoparticles that act as carriers for delivery of peptides such as insulin.

WO2014/125256 describes nanoparticle delivery systems for use in targeting biologically active agents to the central nervous system (CNS), e.g., for treatment of CNS disorders.

Setua et al., 2014, *Nanoscale*, Vol. 6(18), pp. 10865-10873, describes Cisplatin-tethered gold nanospheres for multimodal chemo-radiotherapy of glioblastoma.

Cui et al., 2013, *Nanomedicine: Nanotechnology, Biology, and Medicine*, Vol. 9, pp. 264-273, describes neoplastic cell response to tiopronin-coated gold nanoparticles.

Schaeublin et al., 2011, *Nanoscale*, Vol. 3, pp. 410-120, investigated the influence of surface charge on gold nanoparticle-mediated toxicity.

There remains an unmet need for further therapeutic agents for treatment of cancers, such as SCC, either alone or in combination with radiotherapy. The present invention addresses these and other needs.

BRIEF DESCRIPTION OF THE INVENTION

Broadly, the present invention relates to use of nanoparticles as anticancer agents. The present inventors have surprisingly found that gold core nanoparticles with a mixed corona of covalently attached ligands (alpha-galactose and PEGamine) exhibit selective toxicity in clonogenic assays, killing tumour cell lines, but sparing a non-cancer control cell line. The anticancer activity was exhibit in the absence of any added "payload" of cytotoxic agent. Indeed, without wishing to be bound by any particular theory, the present inventors believe that the mechanism of cell killing may involve production of nanoparticle-mediated production of reactive oxygen species. The results described herein indicate that cancer cell killing was potentiated by radiotherapy.

Accordingly, in a first aspect the present invention provides a nanoparticle comprising a core comprising a metal; and a corona comprising a plurality of ligands covalently linked to the core, the plurality of ligands including at least a first species of ligand comprising an ethylene glycol portion and an amine group and at least a second species of ligand comprising a carbohydrate group, for use in a method of treating a cancer in a mammalian subject.

In some cases in accordance with this and other aspects of the present invention, said first species of ligand may comprise an amine-functionalised poly(ethylene glycol) or amine-functionalised oligo(ethylene glycol). In some cases the first species of ligand may comprise C2-C15 alkyl (e.g. C2, C3, C4, C5, C6, C7, C8, C9, C10, C11, C12, C13, C14 or C15, whether straight or branched-chain) and/or C2-C15 glycol (e.g. C2, C3, C4, C5, C6, C7, C8, C9, C10, C11, C12, C13, C14 or C15). Preferably, the amino group is a terminal amine at the end of the ligand that is other than the end bound to the core of the nanoparticle. In some cases, said first species of ligand comprises an amine-functionalised hexaethylene glycol. In particular, the first species of ligand comprises a ligand according to formula (I):

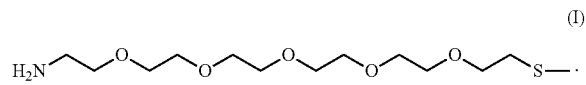 [SMILES: CSCCOCCOCCOCCOCCOCCN]

(I)

In some cases in accordance with this and other aspects of the present invention, said second species of ligand may comprise a monosaccharide, an oligosaccharide or a polysaccharide. In some cases, said second species of ligand comprises galactose, glucose or N-acetylglucosamine. In some cases, said second species of ligand comprises glucose, alpha galactose, mannose, fucose, maltose, lactose, galactosamine and/or N-acetylglucosamine. In particular cases, said second species of ligand comprises alpha-galactose. In particular cases, said second species of ligand comprises alpha-galactose covalently linked to said core via a thioethyl group. In some cases in accordance with the present invention said second species of ligand comprises 2'-thioethyl-β-D-glucopyranoside or 2'-thioethyl-α-D-glucopyranoside covalently attached to the core via the thiol sulphur atom.

The first and/or second species of ligand may be bound to the to the surface atom(s) of the nanoparticle core (e.g. a gold core) via a linker. In some cases, the linker may comprise a sulphur-containing group, an amino-containing group, a phosphate-containing group or an oxygen-containing group. In particular cases, the linker comprises a thiol group and the ligand or ligands are bound to the core via a sulphur-core bound (e.g., for a gold-containing core, the bond may be a gold-sulphur, gold-thiol or gold-sulphide bond). In some cases the linker may comprise a thioethyl group or a thiopropyl group. In certain cases, the nanoparticle may have the general structure as depicted in FIG. 1.

In some cases in accordance with the present invention, the nanoparticle comprises at least 1, 2, 3, 4, 5, 6, 7, 8, 9, 10, at least 20, at least 30, at least 40 or at least 50 ligands. In certain cases, the number of said first species of ligand may be 1, 2, 3, 4, 5, 6, 7, 8, 9, 10, at least 20, at least 30, at least 40 or at least 50. In certain cases, the number of said second species of ligand may be 1, 2, 3, 4, 5, 6, 7, 8, 9, 10, at least 20, at least 30, at least 40 or at least 50.

As described in the Examples herein, the present inventors have found that the ratio of the first and second species of ligand may in some cases influence the activity, e.g. cancer cell killing activity of the nanoparticles. A hexaethyleneglycol (EG)6-amine:alpha-galactose gold nanoparticle having the EG6-amine:alpha-galactose ligands in the ratio of approximately 40:60 exhibited particularly high cell killing activity against HSC-3 cells as assessed by clonogenic assay.

Moreover, gold nanoparticles having the EG6-amine:alpha-galactose ligands in the ratio of approximately 80:20, 40:60 and 20:80 also exhibited robust cell killing activity against HSC-3 cells as assessed by clonogenic assay. Accordingly, in certain cases said first and second species of ligands may be present on the nanoparticle of this and other aspects of the present invention in a molar ratio in the range 95:5 to 5:95 (i.e. 95 glycol-amine containing ligands to 5 carbohydrate-containing ligands), or 80:20 to 20:80, or 60:40 to 40:60. In particular, cases said first and second species of ligands may be present at a ratio in the range 30:70 to 50:50 or 55:45 to 45:55. The ratio of ligands may be determined by methods of analysis known to the skilled person, including, for example, $^1$H-NMR and/or UV spectroscopy. Moreover, the ratio of different species of ligand on the nanoparticle is generally directly influenced by the ratio of ligands present during synthesis of the nanoparticles. As described in Example 1, the ratio of thiol-EG6-amine and thiol-C2-alpha-galactose ligands was 1:1 and resulted in nanoparticles having the two species of ligand present on the nanoparticle in a ratio of approximately 1:1.

The inventors of the present invention surprisingly found that the nanoparticles described herein exhibit cell killing activity against cancer cell lines (HSC-3 and HeLa) even in the absence of a "conventional" cytotoxic drug or payload. Thus, while cisplatin-tethered gold nanoparticles having been proposed for chemo-radiotherapy of glioblastoma (Setua et al., 2014, *Nanoscale*, Vol. 6(18), pp. 10865-10873), this is to our knowledge the first report of an anticancer effect by "payload-free" nanoparticles, even in the absence of radiotherapy or hysteresis-induced killing. Accordingly, in certain cases the nanoparticle of this and other aspects of the present invention may only have ligands covalently linked to the core which are said first species of ligand and said second species of ligand. In particular, the nanoparticle of this and other aspects of the present invention may in certain cases not have any cytotoxic drug or toxin bound to the nanoparticle core or coronal surface. In certain cases the ligands of the nanoparticle of this and other aspects of the present invention may consist of said first and said second species of ligands.

In some cases in accordance with the present invention the diameter of the core of the nanoparticle is in the range 1 nm to 5 nm.

In some cases in accordance with the present invention the diameter of the nanoparticle including its ligands is in the range 3 nm to 20 nm, optionally 4 nm to 15 nm or 4 nm to 5 nm.

In accordance with the present invention the nanoparticle of the invention may comprise a component having a divalent state, such as a metal or a compound having a divalent state, or an oxide or salt thereof. For example, metals or metal complexes having the ability to exist in a divalent state are particularly useful. Such a component may be in the divalent state as added or may be transformed into a divalent state after addition. Oxides and salts of the divalent component are also useful and may be added directly or formed in situ subsequent to addition. Among the useful salts of the divalent component include halide salts, such as chloride, iodide, bromide and fluoride. Such divalent components may include, for example, zinc, magnesium, copper, nickel, cobalt, cadmium, or calcium, and their oxides and salts thereof. The component is desirably present in an amount sufficient to enhance cancer cell killing to a level greater than the level of cancer cell killing by the nanoparticle in the absence of the component having a divalent state. In some cases, the component having a divalent state is desirably present in an amount of about 0.5 to 2.0 equivalents to the core metal (e.g. gold), or optionally about 0.75 to 1.5 equivalents to the core metal (e.g. gold). In the context of the present invention, "equivalents" may be mole equivalents, for example 1.0 equivalent of zinc may be taken to mean the same number of zinc atoms or $Zn^{2+}$ cations as the number of gold atoms in the core of the nanoparticle.

The divalent component may in some cases be present in the corona of the nanoparticle. It is specifically contemplated herein that the divalent component may be included in the nanoparticle, including in the corona of the nanoparticle as a result of inclusion of the divalent component in the process of synthesis of the nanoparticle. Additionally or alternatively, the divalent component may be added after synthesis of the nanoparticle. In some cases in accordance with the present invention, the divalent component, such as zinc may be selected from: $Zn^{2+}$ and ZnO. For example, the zinc may be in the form of $ZnCl_2$.

Alternatively, the nanoparticle or composition comprising the nanoparticle may in some cases be substantially free of $Zn^{2+}$ ions.

In some cases in accordance with the present invention the core comprises a metal selected from the group consisting of: Au, Ag, Cu, Pt, Pd, Fe, Co, Gd, Eu and Zn, or any combination thereof.

In some cases in accordance with the present invention the core is magnetic.

In some cases in accordance with the present invention the core comprises a semiconductor. In particular, the semiconductor may in some cases be selected from the group consisting of: cadmium selenide, cadmium sulphide, cadmium tellurium and zinc sulphide.

In some cases in accordance with the present invention the core is capable of acting as a quantum dot.

In certain cases, the nanoparticle of this and other aspects of the present invention may be for use in the treatment of a cancer selected from the group consisting of: squamous cell carcinoma (SCC), cervical cancer, skin cancer, oral cancer, glioma, lung cancer, bladder cancer, ocular cancer, stomach cancer, and esophageal cancer. The cancer may be a solid tumour. In some cases, the cancer may comprise a tumour which is amenable to treatment via direct application of the nanoparticle to the tumour and/or surrounding tissue, e.g., via topical administration. Anti-cancer activity has been observed against an oral SCC-derived cell line (HSC-3) and against a cervical cancer cell line (HeLa cells) —see Examples herein. Moreover, without wishing to be bound by any particular theory, the present inventors believe that the mechanism of cancer cell killing induced by the nanoparticles described herein may involve production of reactive oxygen species, which would be expected to make the nanoparticles of the invention potentially applicable to a wide variety of different cancers. In particular cases, said cancer is oral SCC (e.g. tongue SCC) or skin SCC.

As described further in the Examples herein, the cell killing effect on cancer cells was potentiated by subjecting cells treated with the nanoparticles described herein also to x-ray radiation.

Accordingly, the nanoparticles of this and other aspects of the present invention may be for use in a method of treating said cancer which further comprises administering radiotherapy to the subject. In some cases said method of treating said cancer comprises administering said nanoparticle and subsequently or concurrently administering said radiotherapy to the subject. Preferably the radiotherapy is applied at a point in time in which said nanoparticles remain at an appropriate concentration at the site of the tumour or the immediate vicinity of the tumour. In cases where the nanoparticles comprise a gold- or platinum-containing core, x-ray radiation is thought to emit Auger electrons that are able to damage and/or kill cells. In accordance with the present invention, said radiotherapy may comprises x-ray radiation, e.g. external beam x-ray radiation.

In a second aspect the present invention provides a pharmaceutical composition for use in a method in accordance with the first aspect of the invention, the composition comprising one or more nanoparticles in accordance with the first aspect of the invention and a pharmaceutically acceptable carrier, excipient or diluent. In some cases, in accordance with any one of the aspects of the present invention, the nanoparticle pharmaceutical composition comprises a carrier, such as solution, a polymer, a powder, or a cream, in which the nanoparticles are suspended. The composition may be in an associated form, a suspension or contained together in a single package, container or carrier. In certain cases, the composition may take the form of one or more doses (e.g. a defined quantity of nanoparticles or defined quantity of anti-cancer activity units), such as in the form of a therapeutic dose or defined number of doses.

In some cases, in accordance with this aspect of the present invention, the nanoparticle pharmaceutical composition may further comprises at least one permeation enhancer. Certain permeation enhancers may be advantageously bound to the nanoparticle or otherwise present in the composition and provide enhanced cell or tissue penetration. In certain cases, said permeation enhancer is selected from: N-lauroylsarcosine, sobitan monolaurate ("Span® 20"), an alkyl-D-maltoside (e.g. tetradecyl-D-maltoside, dodecyl-β-D-maltoside, hexyl-β-D-maltoside, octyl-β-D-maltoside, nonyl-β-D-maltoside, decyl-β-D-maltoside, undecyl-β-D-maltoside, tridecyl-β-D-maltoside, or hexadecyl-β-D-maltoside) and lysalbinic acid.

In accordance with this aspect of the invention, the nanoparticle pharmaceutical composition may be administered or for administration by any suitable route. In particular cases, the nanoparticle pharmaceutical composition may be administered or for administration via a route selected from the group consisting of: topical, intravenous (i.v.), intramuscular (i.m.), intradermal (i.d.), intraperitoneal or subcutaneous (s.c.) injection or infusion; buccal; sublabial; sublingual; by inhalation; via one or more mucosal membranes; urogenital; rectal; and dermal. In certain cases, the nanoparticle pharmaceutical composition may be formulated for topical administration or may be administered topically. In particular cases, the nanoparticle pharmaceutical composition may be for topical administration to a skin or oral SCC tumour and/or surrounding tissue or may be administered topically to a skin or oral SCC tumour and/or surrounding tissue.

In a third aspect, the present invention provides use of a nanoparticle of the first aspect of the invention or a pharmaceutical composition of the second aspect of the invention in the preparation of a medicament for the treatment of a cancer. The cancer may be as defined in accordance with the first aspect of the invention. In some cases said cancer is selected from the group consisting of: squamous cell carcinoma (SCC), cervical cancer, skin cancer, oral cancer, glioma, lung cancer, bladder cancer, ocular cancer, stomach cancer, and esophageal cancer. In certain cases, said cancer is oral or skin SCC.

In some cases in accordance with this aspect of the invention, said medicament is for treating said cancer in combination with radiotherapy. The radiotherapy may be as defined in accordance with the first aspect of the invention.

In a fourth aspect, the present invention provides a method of treatment of a cancer in a subject in need thereof, said method comprising administering a therapeutically effective amount of a nanoparticle as defined in accordance with the first aspect of the invention or a pharmaceutical composition as defined in accordance with the second aspect of the invention to said subject. The cancer may be as defined in accordance with the first aspect of the invention. In some cases said cancer is selected from the group consisting of: squamous cell carcinoma (SCC), cervical cancer, skin cancer, oral cancer, glioma, lung cancer, bladder cancer, ocular cancer, stomach cancer, and esophageal cancer. In certain cases, said cancer is oral or skin SCC.

In some cases in accordance with this aspect of the invention, said method further comprises administering radiotherapy to said subject. The radiotherapy may be as defined in accordance with the first aspect of the invention.

In a fifth aspect, the present invention provides an article of manufacture comprising:
 a nanoparticle as defined in accordance with the first aspect of the invention or a pharmaceutical composition as defined in accordance with the second aspect of the invention;
 a container for housing the nanoparticle or pharmaceutical composition; and
 and insert or label with administration and/or dosage instructions for the treatment of a cancer. The cancer may be as defined in accordance with the first aspect of the invention. In some cases said cancer is selected from the group consisting of: squamous cell carcinoma (SCC), cervical cancer, skin cancer, oral cancer, glioma, lung cancer, bladder cancer, ocular cancer, stomach cancer, and esophageal cancer. In certain cases, said cancer is oral or skin SCC.

In accordance with any aspect of the present invention, the subject may be a human, a companion animal (e.g. a dog or cat), a laboratory animal (e.g. a mouse, rat, rabbit, pig or non-human primate), a domestic or farm animal (e.g. a pig, cow, horse or sheep). Preferably, the subject is a human. In particular, the subject may be suffering from, diagnosed with or assessed as having a risk of developing, a cancer, including a cancer as defined in accordance with the first aspect of the invention.

The present invention includes the combination of the aspects and preferred features described except where such a combination is clearly impermissible or is stated to be expressly avoided. These and further aspects and embodiments of the invention are described in further detail below and with reference to the accompanying examples and figures.

Figure 3:
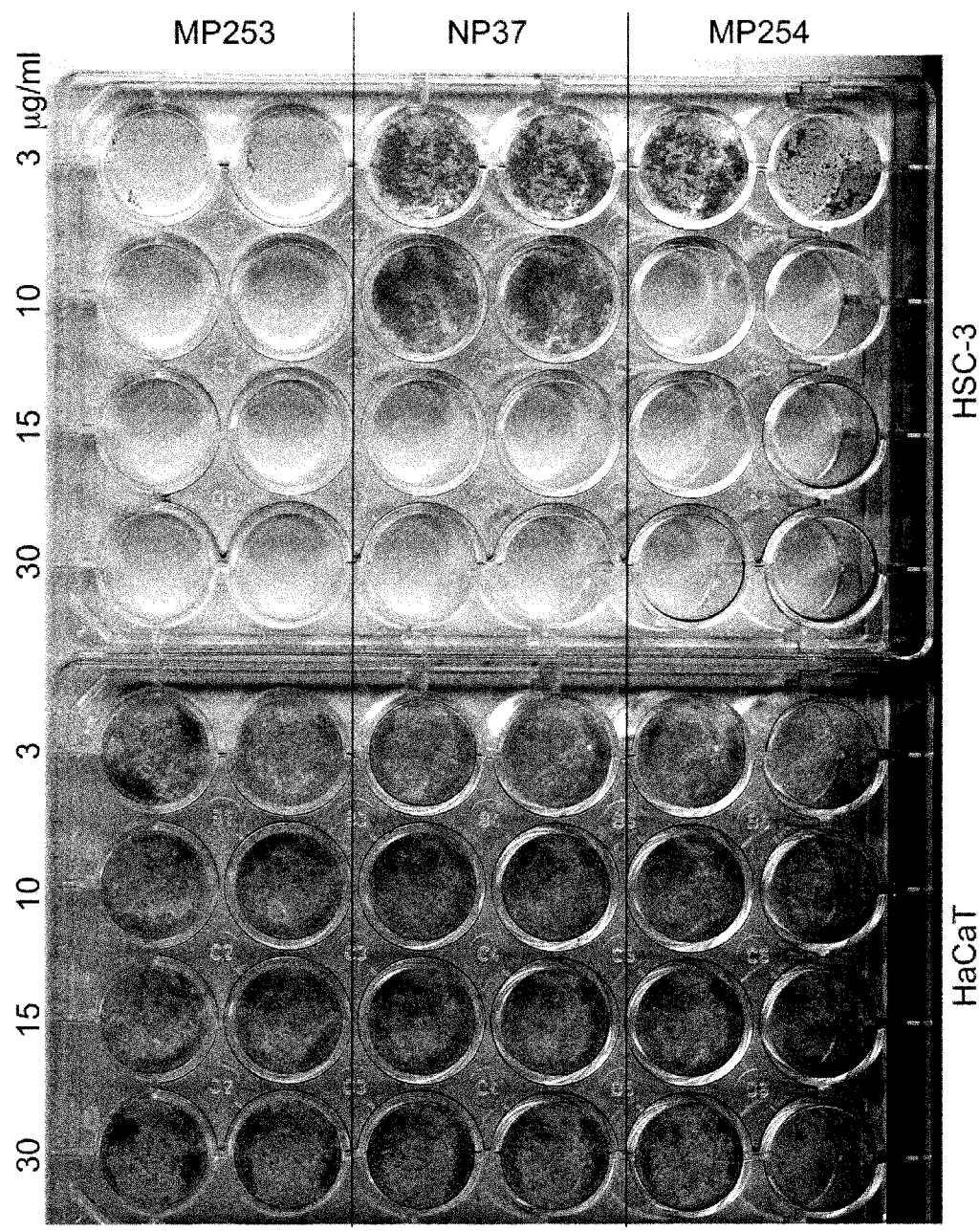

FIG. 3 shows clonogenic assay duplicate results in the form of a photograph of two 24-well plates, in which: HSC-3 (upper plate) and HaCaT (lower plate) cells were treated with 3 (row 1), 10 (row 2), 15 (row 3) and 30 (row 4) µg/ml of MP253 (60:40 alpha-galactose-C2:PEGamine-GNP; columns 1 and 2), NP37 (50:50 alpha-galactose-C2:PEGamine-GNP; columns 3 and 4), and MP254 (40:60 alpha-galactose-C2:PEGamine-GNP; columns 5 and 6) nanoparticles. Plates were seeded with 500 cells/well and nanoparticles were applied for 3 hours, then washed out and replaced with fresh medium, then left for 7 days. The results show cell killing for HSC-3 cells by all three nanoparticle types in comparison to HaCaT cells. The order of potency (highest to lowest) was MP253>MP254>NP37.

Figure 4:
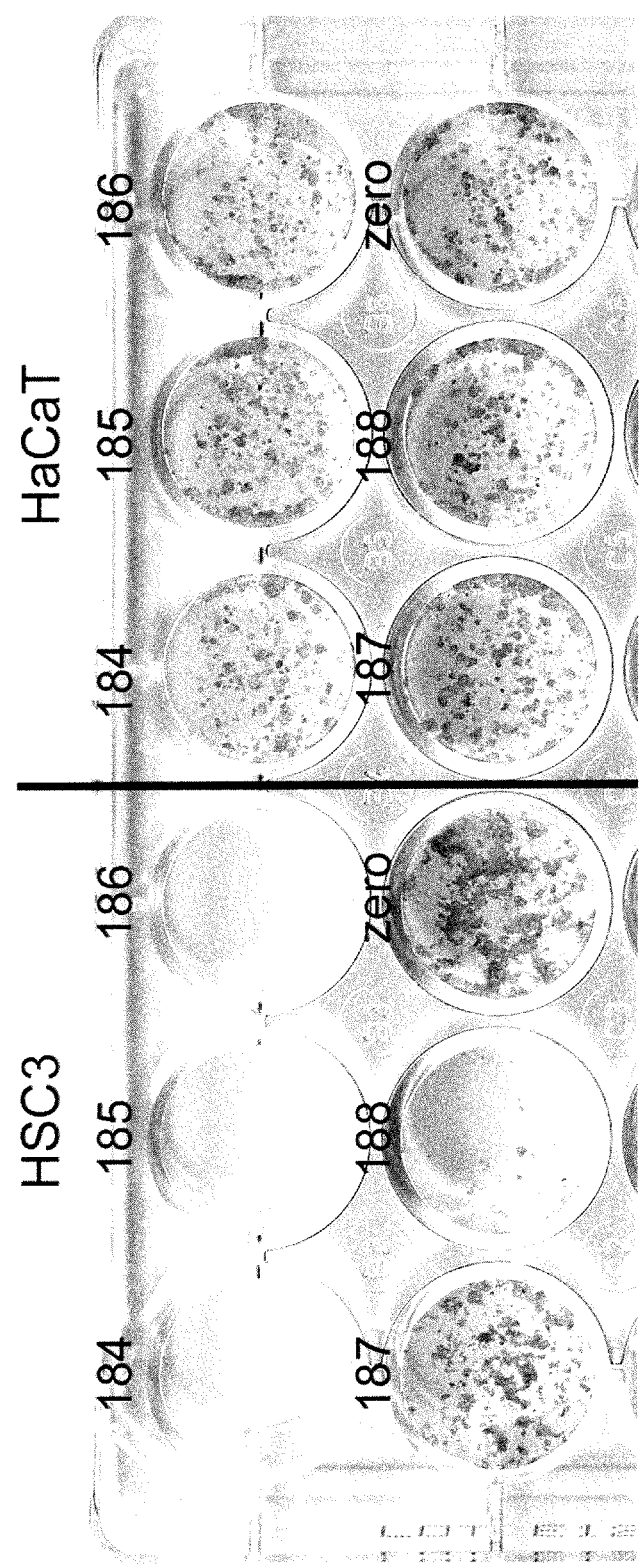

FIG. 4 shows clonogenic assay results of various nanoparticles to HSC-3 cells (columns 1, 2 and 3) and HaCaT cells (columns 4, 5 and 6). All nanoparticle treatments were at 15 µg/ml for 3 hours. The top row treatments were (left to right): MP184 (50:50 alpha-galactose-C2:PEGamine-GNP), MP185 (50:50 beta-glucose-C2:PEGamine-GNP) and MP186 (50:50 N-acetyl-glucosamine-C2:PEGamine-GNP). The lower row treatments were (left to right): MP187 (100% alpha-galactose-C2-GNP), MP188 (100% PEGamine-GNP) and untreated control "zero". The results show clear cell killing of HSC-3 cells in comparison to HaCaT cells by MP184, MP185, MP186 and MP188 at the concentration tested.

Figure 5:
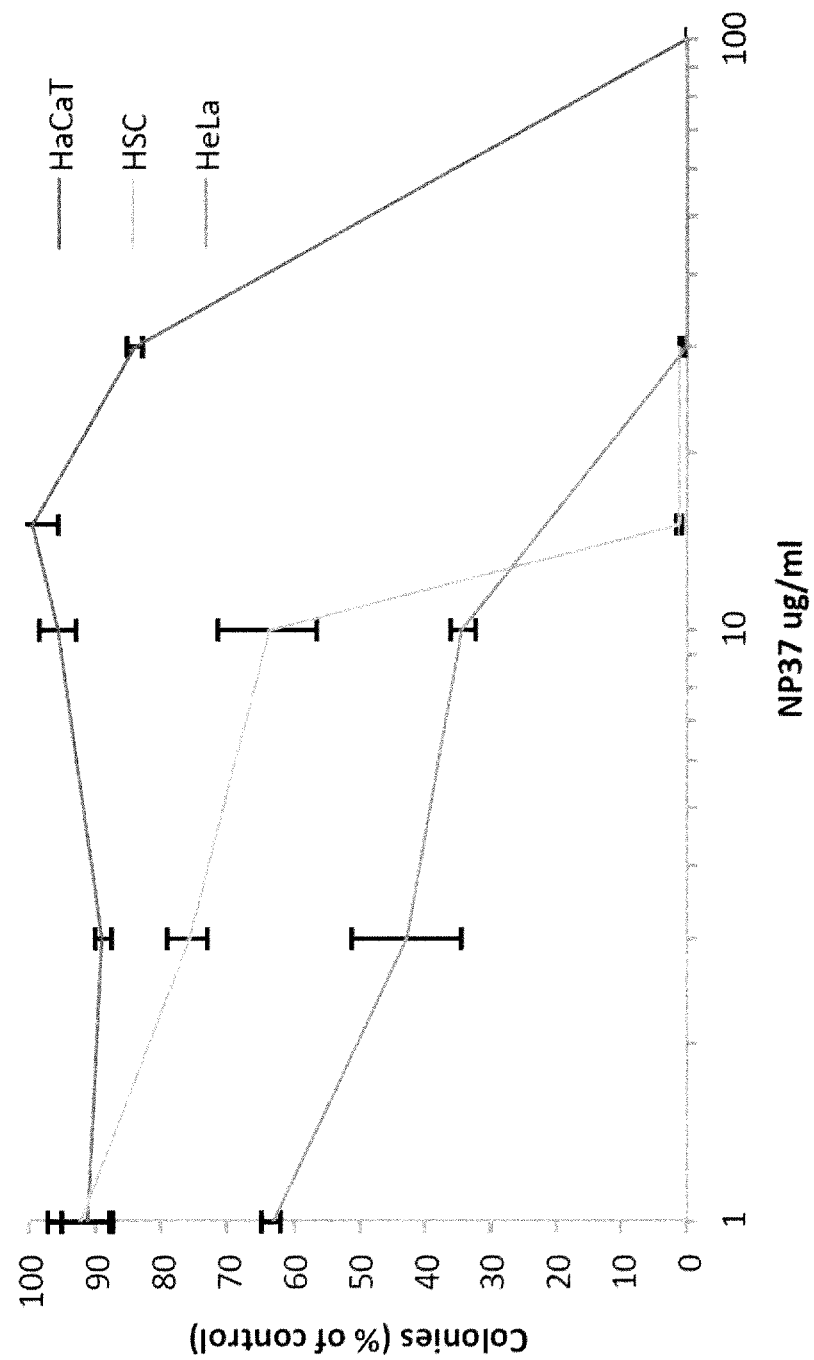

FIG. 5 shows a dose-response curve (colonies % control vs. concentration of NP37 nanoparticles µg/ml) derived from clonogenic assay results with three cell lines: HaCaT (upper line; red); HSC-3 (middle line, crossing to lower line above 10 µg/ml; green); and HeLa (lower line, crossing to middle line above 10 µg/ml; blue). The cells were incubated for 6 hours with NP37 nanoparticles at 1, 3, 10, 30 and 100 µg/ml. The data points at 15 µg/ml NP37 nanoparticles were from a separate experiment which used a 3-hour incubation time with NP37 nanoparticles.

Figure 6:
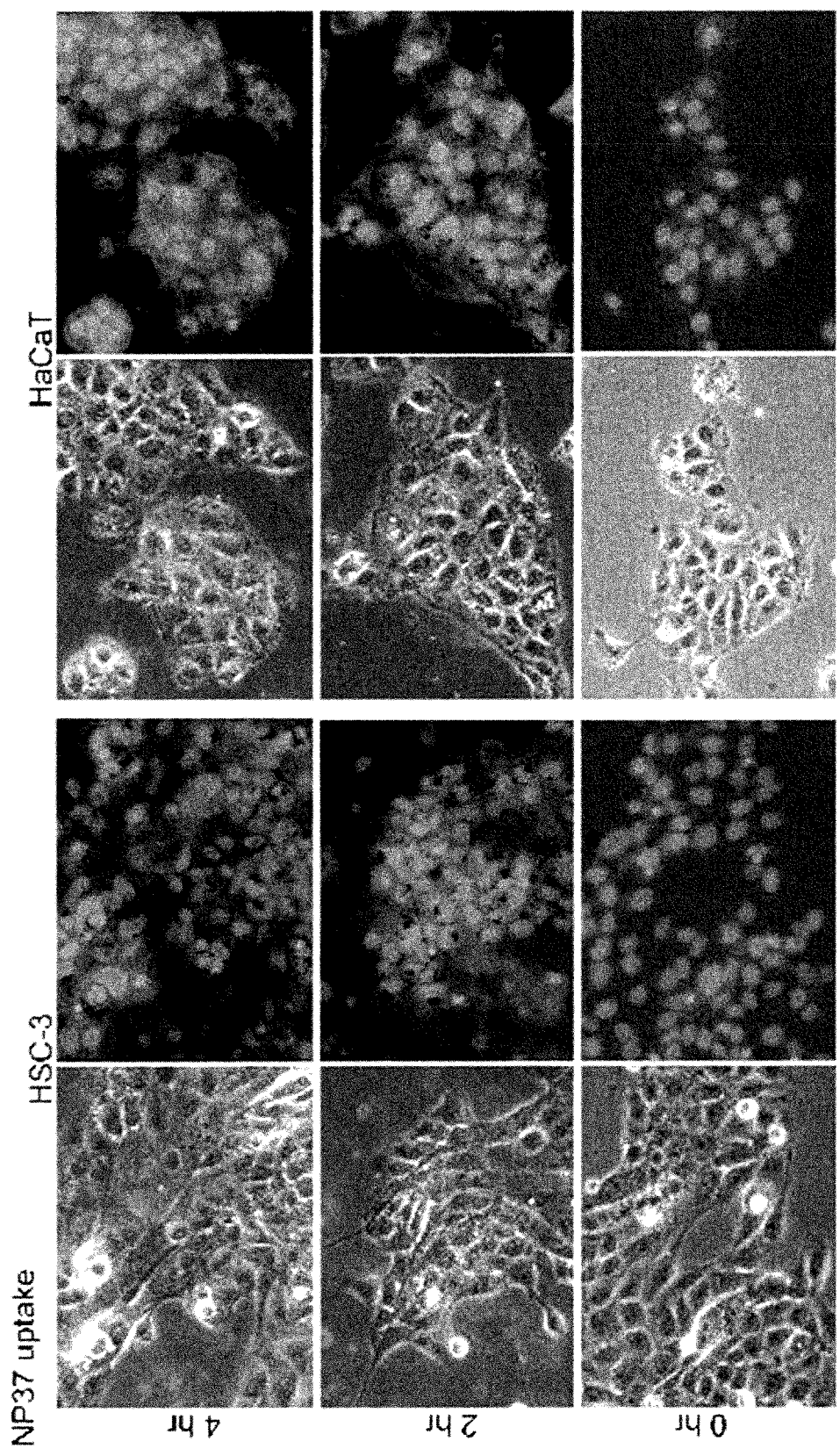

FIG. 6 shows micrographs with silver enhancement of cellular uptake of NP37 nanoparticles. The black dots show gold nanoparticles; the bright green is a nuclear stain. Results are shown for HSC-3 cells and HaCaT cells at time zero (0 hours), 2 hours and 4 hours after treatment with NP37 nanoparticles. The results show accumulation of NP37 nanoparticles into cells, adjacent to the cell nucleus, which may represent accumulation within the Golgi.

Figure 7:
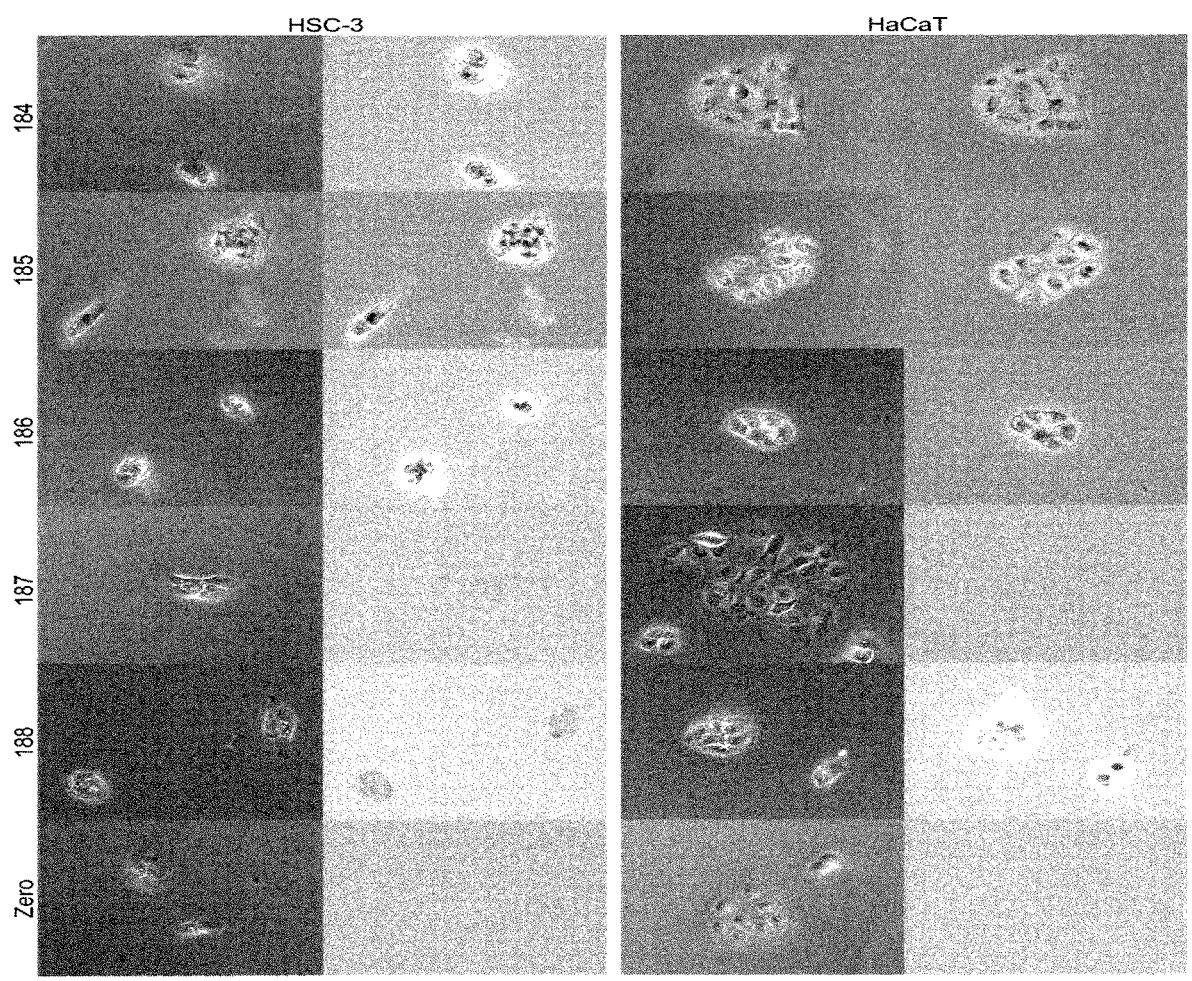

FIG. 7 shows silver enhancement images for acute (3-hour) uptake of nanoparticles by HSC-3 (left) and HaCaT cells (right). The paired images show phase (left) and bright field (right). The nanoparticles treatments (all 15 µg/ml) were (top to bottom): MP184 (50:50 alpha-galactose-C2:PEGamine-GNP), MP185 (50:50 beta-glucose-C2:PEGamine-GNP), MP186 (50:50 N-acetyl-glucosamine-C2:PEGamine-GNP), MP187 (100% alpha-galactose-C2-GNP), MP188 (100% PEGamine-GNP), and zero (untreated control). The results indicate greater cell uptake of MP184-186, with lower uptake of MP187 and MP188. The location of the majority of the staining was found to be juxtanuclear.

Figure 8:
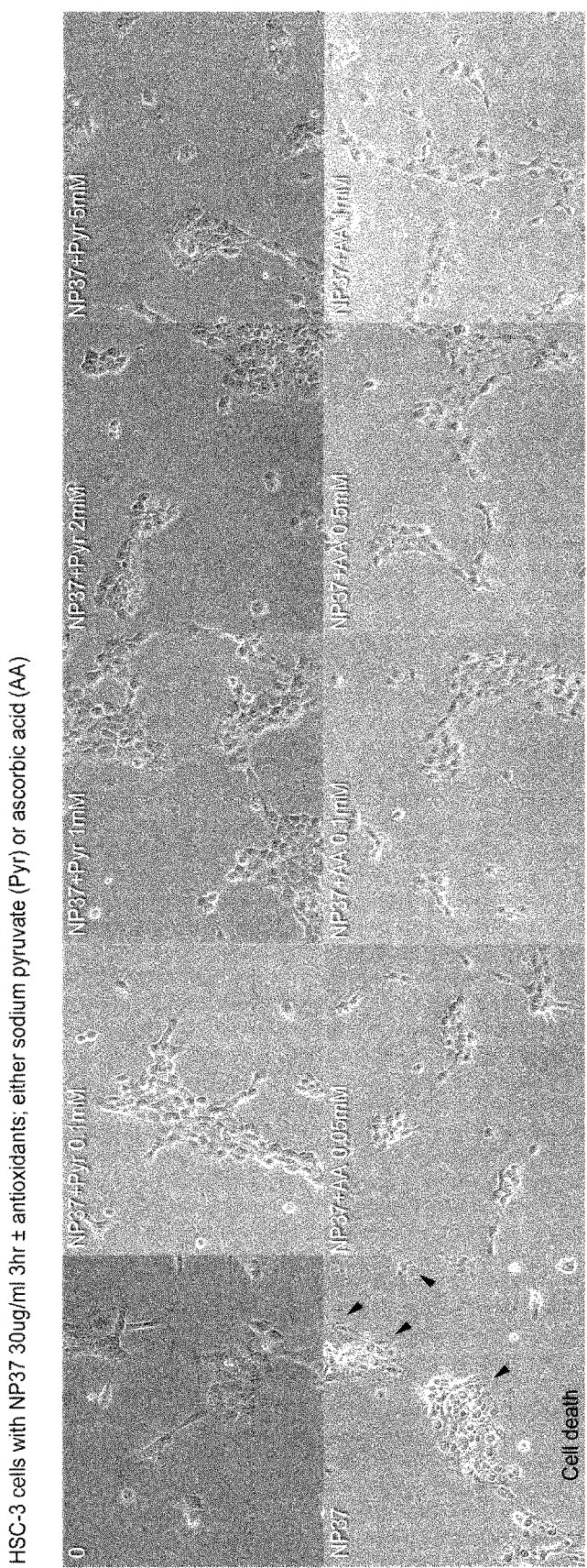

FIG. 8 shows micrograph images of HSC-3 cells treated with NP37 nanoparticles (30 µg/ml for 3 hours) in the presence or absence of either sodium pyruvate (Pyr) of ascorbic acid (AA) as antioxidants. The Pyr concentrations tested were (left to right): zero, 0.1 mM, 1 mM, 2 mM and 5 mM. The AA concentrations tested were (left to right): zero, 0.05 mM, 0.1 mM, 0.5 mM and 1 mM. The results indicate that both antioxidant treatments were able to prevent NP37-mediated cell death of HSC-3 cells.

Figure 9:
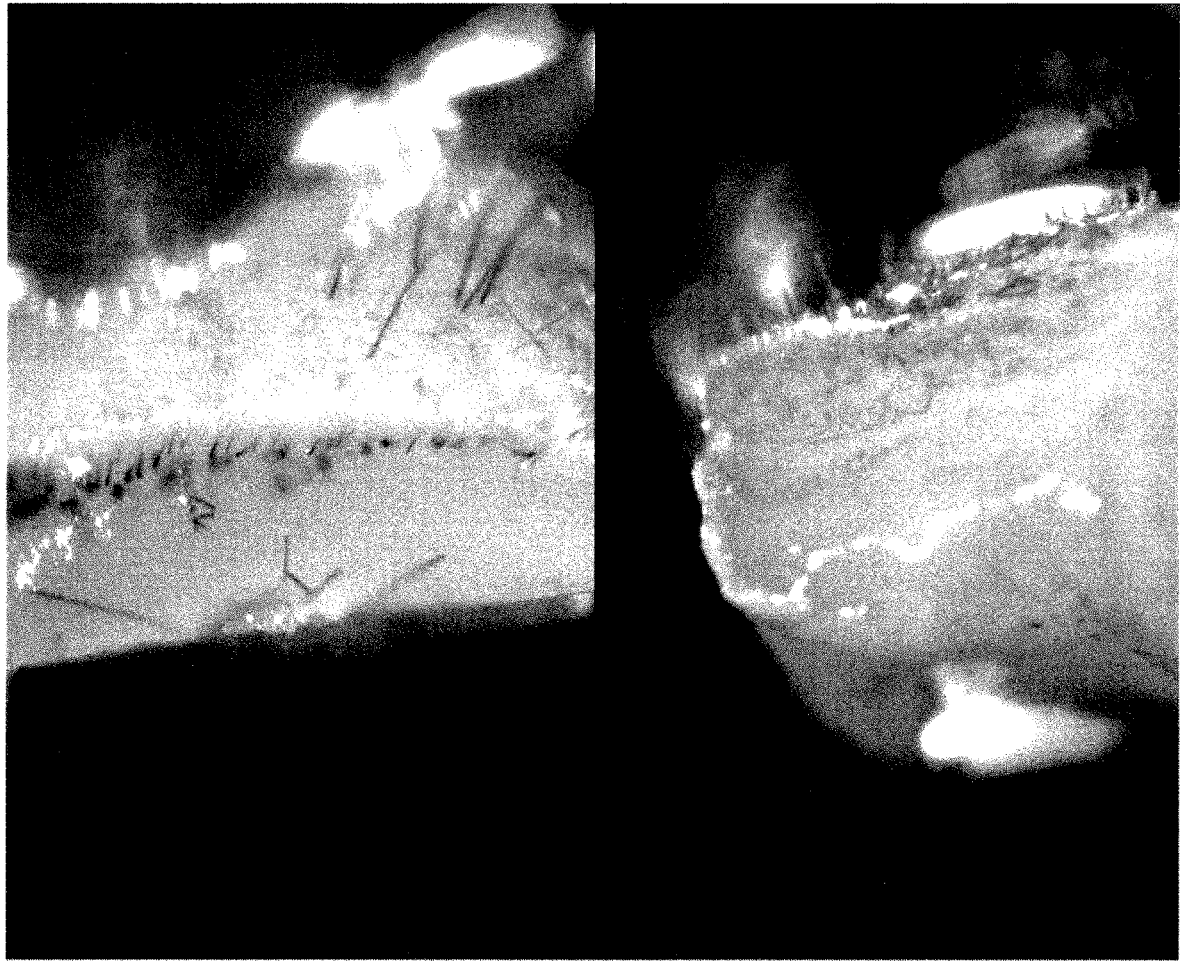

FIG. 9 shows NP37 nanoparticle murine skin penetration following 200 µg/ml topical application of nanoparticles for 4 hours. The skin section was fixed and stained with silver enhancer. The images show untreated control (left) and NP37 nanoparticles (right). On the left-hand image the black regions within the skin are melanin. On the right-hand image, the silver staining reveals the gold nanoparticles as an even grey/green stain, which is distinct from melanin. The results suggest penetration of murine skin by NP37 nanoparticles.

Figure 10:
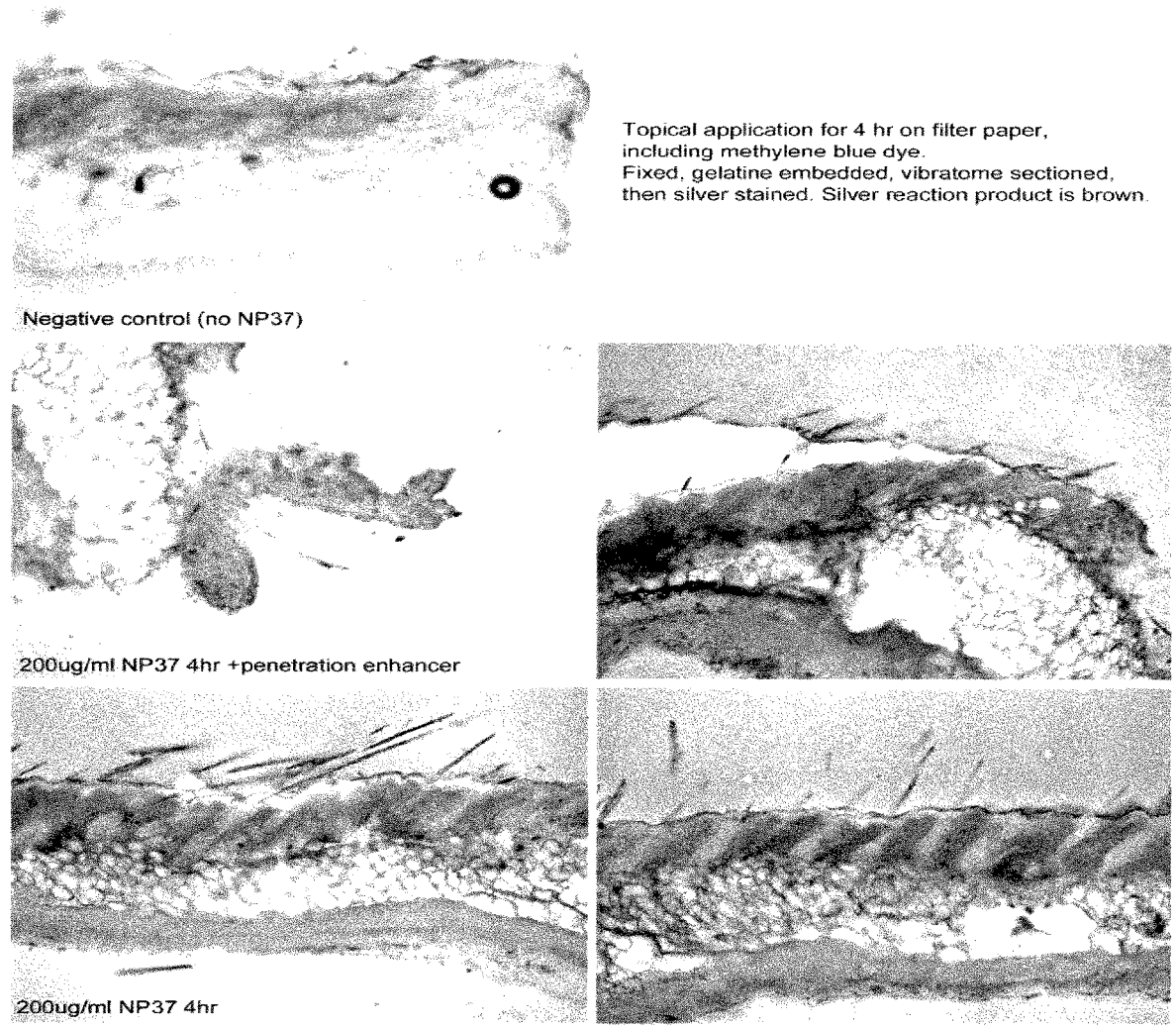

FIG. 10 shows NP37 nanoparticle skin penetration following 200 µg/ml topical application of nanoparticles for 4 hours. The skin samples were fixed, gelatine embedded, vibratome sectioned, then silver stained. The silver reaction product is brown. The upper row shows untreated control. The middle row shows skin treated with 200 µg/ml NP37+ penetration enhancer (60 mg N-lauroylsarcosine and 40 mg sorbitan monolaurate (Span® 20) per 10 ml of phosphate buffer:ethanol (1:1)) for 4 hours. The bottom row shows 200 µg/ml NP37 for 4 hours. The results indicate that NP37 nanoparticles are rapidly absorbed into murine skin.

Figure 11:
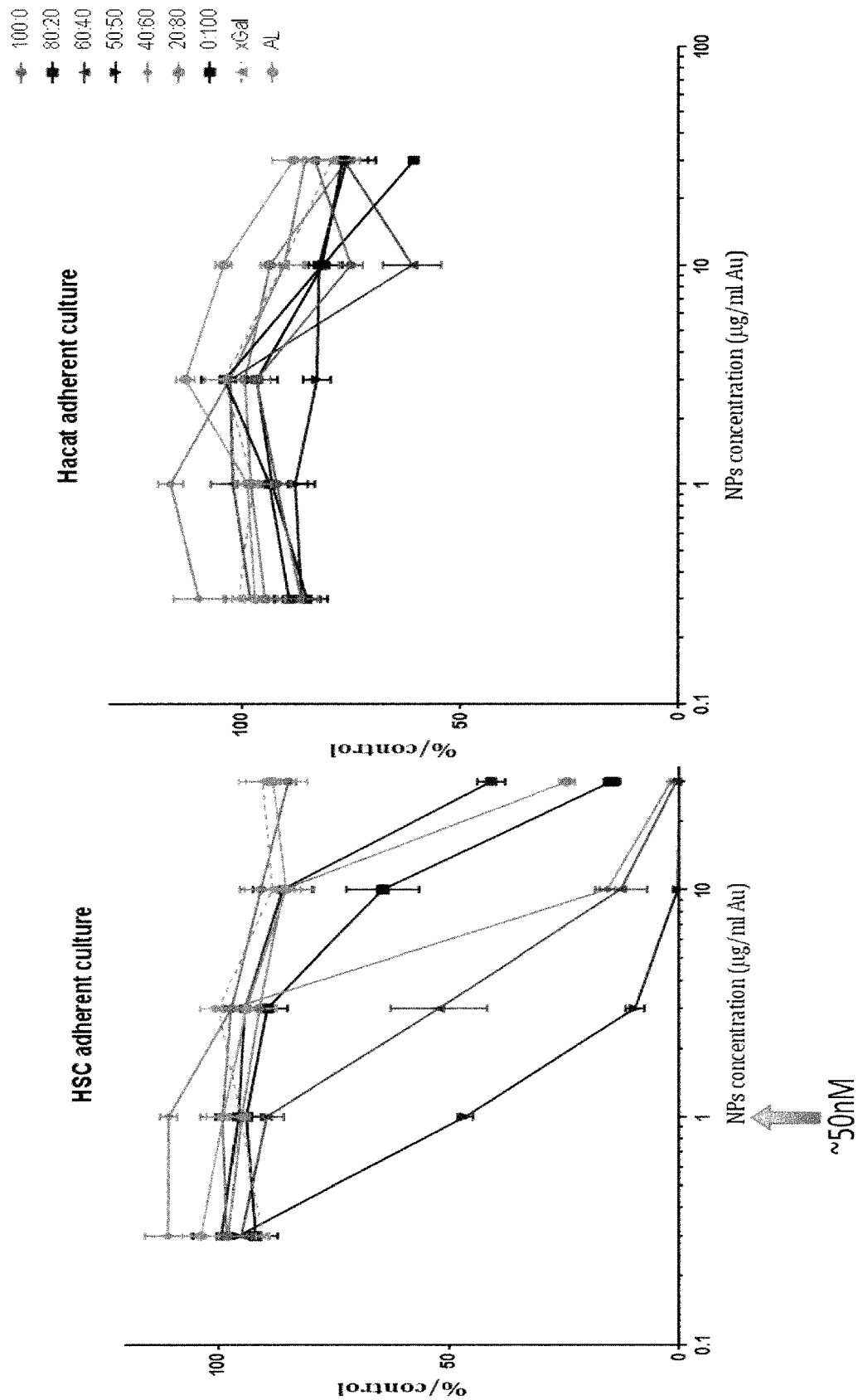

FIG. 11 shows dose-dependent toxicity (% control surviving) of various ratios of sugar:PEGamine nanoparticles against HSC-3 Oral SCC cells (left-hand panel) and HaCaT control keratinocytes. The key to the right of the right-hand panel shows (from top to bottom): alpha-galactose:PEGamine 100:0 (orange circles); 80:20 (red squares); 60:40 (green triangles); 50:50 (blue inverted triangles); 40:60 (blue diamonds); 20:80 (pink circles); 0:100 (black squares); xGal (grey triangles); and amino linker (AL) (grey circles). The $IC_{50}$ of the 50:50 alpha-galactose:PEGamine nanoparticles was found to be 0.96 µg/ml (approximately 50 nM), which is much lower than the $IC_{50}$ measured for the same nanoparticles against the HaCaT cells>10000 µg/ml, indicating selective anti-cancer toxicity. The 50:50 ratio alpha-galactose:PEGamine AuNPs were found to exhibit the greatest anti-cancer toxicity, followed by the 60:40 ratio alpha-galactose:PEGamine AuNPs as the next most potent.

Figure 12:
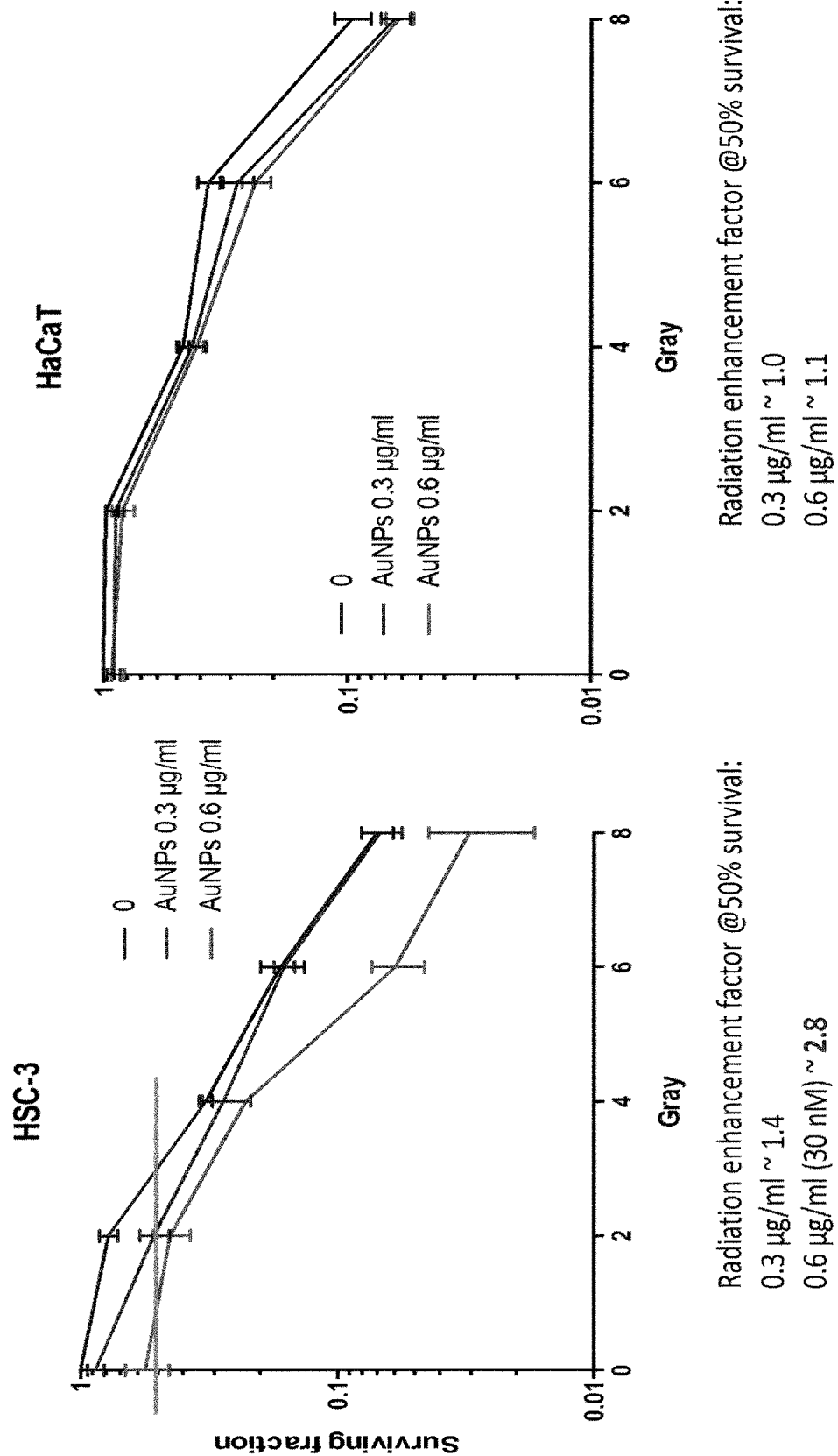

FIG. 12 shows toxicity (surviving fraction; y-axis) plotted against radiation dose (Gray; x-axis) of HSC-3 cells (left-hand panel) and HaCaT cells (right-hand panel) for control (red line; no drug), 0.3 µg/ml gold nanoparticles with a corona of 50:50 alpha-galactose:PEGamine (blue), and 0.6 µg/ml gold nanoparticles with a corona of 50:50 alpha-galactose:PEGamine (green). The nanoparticle-treated HSC-3 cells exhibited enhancement of radiation-induced cell killing (approximately 1.4× for 0.3 µg/ml AuNPs; 2.8× for 0.6 µg/ml AuNPs). A much lower level of radiation potentiation was seen in the non-cancer HaCaT cells (approximately 1.0× for 0.3 µg/ml AuNPs; 1.1× for 0.6 µg/ml AuNPs).

DETAILED DESCRIPTION OF THE INVENTION

In describing the present invention, the following terms will be employed, and are intended to be defined as indicated below.

Nanoparticles

As used herein, "nanoparticle" refers to a particle having a nanomeric scale, and is not intended to convey any specific shape limitation. In particular, "nanoparticle" encompasses nanospheres, nanotubes, nanoboxes, nanoclusters, nanorods and the like. In certain embodiments the nanoparticles and/or nanoparticle cores contemplated herein have a generally polyhedral or spherical geometry.

Nanoparticles comprising a plurality of carbohydrate-containing ligands have been described in, for example, WO 2002/032404, WO 2004/108165, WO 2005/116226, WO 2006/037979, WO 2007/015105, WO 2007/122388, WO 2005/091704 (the entire contents of each of which is expressly incorporated herein by reference) and such nanoparticles may find use in accordance with the present invention.

As used herein, "corona" refers to a layer or coating, which may partially or completely cover the exposed surface of the nanoparticle core. The corona includes a plurality of ligands which generally include at least one carbohydrate moiety, one surfactant moiety and/or one glutathione moiety. Thus, the corona may be considered to be an organic layer that surrounds or partially surrounds the metallic core. In certain embodiments the corona provides and/or participates in passivating the core of the nanoparticle. Thus, in certain cases the corona may include a sufficiently complete coating layer substantially to stabilise the semiconductor or metal-containing core. However, it is specifically contemplated herein that certain nanoparticles having cores, e.g., that include a metal oxide-containing inner core coated with a noble metal may include a corona that only partially coats the core surface. In certain cases the corona facilitates solubility, such as water solubility, of the nanoparticles of the present invention.

Nanoparticles are small particles, e.g. clusters of metal or semiconductor atoms, that can be used as a substrate for immobilising ligands.

Preferably, the nanoparticles have cores having mean diameters between 0.5 and 50 nm, more preferably between 0.5 and 10 nm, more preferably between 0.5 and 5 nm, more preferably between 0.5 and 3 nm and still more preferably between 0.5 and 2.5 nm. When the ligands are considered in addition to the cores, preferably the overall mean diameter of the particles is between 2.0 and 20 nm, more preferably between 3 and 10 nm and most preferably between 4 and 5 nm. The mean diameter can be measured using techniques well known in the art such as transmission electron microscopy.

The core material can be a metal or semiconductor (said semiconductor optionally comprising metal atoms or being an organic semiconductor) and may be formed of more than one type of atom. Preferably, the core material is a metal selected from Au, Fe or Cu. Nanoparticle cores may also be formed from alloys including Au/Fe, Au/Cu, Au/Gd, Au/Fe/Cu, Au/Fe/Gd and Au/Fe/Cu/Gd, and may be used in the present invention. Preferred core materials are Au and Fe, with the most preferred material being Au. The cores of the nanoparticles preferably comprise between about 100 and 500 atoms (e.g. gold atoms) to provide core diameters in the nanometre range. Other particularly useful core materials are doped with one or more atoms that are NMR active, allowing the nanoparticles to be detected using NMR, both in vitro and in vivo. Examples of NMR active atoms include $Mn^{+2}$, $Gd^{+3}$, $Eu^{+2}$, $Cu^{+2}$, $V^{+2}$, $Co^{+2}$, $Ni^{+2}$, $Fe^{+2}$, $Fe^{+3}$ and lanthanides$^{+3}$, or the quantum dots described elsewhere in this application.

Nanoparticle cores comprising semiconductor compounds can be detected as nanometre scale semiconductor crystals are capable of acting as quantum dots, that is they can absorb light thereby exciting electrons in the materials to higher energy levels, subsequently releasing photons of light at frequencies characteristic of the material. An example of a semiconductor core material is cadmium selenide, cadmium sulphide, cadmium tellurium. Also included are the zinc compounds such as zinc sulphide.

In some embodiments, the nanoparticle or its ligand comprises a detectable label. The label may be an element of the core of the nanoparticle or the ligand. The label may be detectable because of an intrinsic property of that element of the nanoparticle or by being linked, conjugated or associated with a further moiety that is detectable. Preferred examples of labels include a label which is a fluorescent group, a radionuclide, a magnetic label or a dye. Fluorescent groups include fluorescein, rhodamine or tetramethyl rhodamine, Texas-Red, Cy3, Cy5, etc., and may be detected by excitation of the fluorescent label and detection of the emitted light using Raman scattering spectroscopy (Y. C. Cao, R. Jin, C. A. Mirkin, Science 2002, 297: 1536-1539).

In some embodiments, the nanoparticles may comprise a radionuclide for use in detecting the nanoparticle using the radioactivity emitted by the radionuclide, e.g. by using PET, SPECT, or for therapy, i.e. for killing target cells. Examples of radionuclides commonly used in the art that could be readily adapted for use in the present invention include $^{99m}Tc$, which exists in a variety of oxidation states although the most stable is $TcO^{4-}$; $^{32}P$ or $^{33}P$; $^{57}Co$; $^{59}Fe$; $^{67}Cu$ which is often used as $Cu^{2+}$ salts; $^{67}Ga$ which is commonly used a $Ga^{3+}$ salt, e.g. gallium citrate; $^{68}Ge$; $^{82}Sr$; $^{99}Mo$; $^{103}Pd$; $^{111}In$ which is generally used as $In^{3+}$ salts; $^{125}I$ or $^{131}I$ which is generally used as sodium iodide; $^{137}Cs$; $^{153}Gd$; $^{153}Sm$; $^{158}Au$; $^{186}Re$; $^{201}Tl$ generally used as a $Tl^{+}$ salt such as thallium chloride; $^{39}Y^{3+}$; $^{71}Lu^{3+}$; and $^{24}Cr^{2+}$. The general use of radionuclides as labels and tracers is well known in the art and could readily be adapted by the skilled person for use in the aspects of the present invention. The radionuclides may be employed most easily by doping the cores of the nanoparticles or including them as labels present as part of ligands immobilised on the nanoparticles.

Administration and Treatment

The nanoparticles and compositions of the invention may be administered to patients by any number of different routes, including enteral or parenteral routes. Parenteral administration includes administration by the following routes: intravenous, cutaneous or subcutaneous, nasal, intramuscular, intraocular, transepithelial, intraperitoneal and topical (including dermal, ocular, rectal, nasal, inhalation and aerosol), and rectal systemic routes.

The nanoparticles of the invention may be formulated as pharmaceutical compositions that may be in the forms of solid or liquid compositions. Such compositions will generally comprise a carrier of some sort, for example a solid carrier or a liquid carrier such as water, petroleum, animal or vegetable oils, mineral oil or synthetic oil. Physiological saline solution, or glycols such as ethylene glycol, propylene glycol or polyethylene glycol may be included. Such compositions and preparations generally contain at least 0.1 wt % of the compound.

For intravenous, cutaneous or subcutaneous injection, or injection at the site of affliction, the active ingredient will be in the form of a parenterally acceptable aqueous solution or liquid which is pyrogen-free and has suitable pH, isotonicity and stability. Those of relevant skill in the art are well able to prepare suitable solutions using, for example, solutions of the compounds or a derivative thereof, e.g. in physiological saline, a dispersion prepared with glycerol, liquid polyethylene glycol or oils.

In addition to one or more of the compounds, optionally in combination with other active ingredient, the compositions can comprise one or more of a pharmaceutically acceptable excipient, carrier, buffer, stabiliser, isotonicising agent, preservative or anti-oxidant or other materials well known to those skilled in the art. Such materials should be non-toxic and should not interfere with the efficacy of the active ingredient. The precise nature of the carrier or other material may depend on the route of administration, e.g., intramuscular injection.

Preferably, the pharmaceutically compositions are given to an individual in a prophylactically effective amount or a therapeutically effective amount (as the case may be, although prophylaxis may be considered therapy), this being sufficient to show benefit to the individual. Typically, this will be to cause a therapeutically useful activity providing benefit to the individual. The actual amount of the compounds administered, and rate and time-course of administration, will depend on the nature and severity of the condition being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Handbook of Pharmaceutical Additives, 2nd Edition (eds. M. Ash and I. Ash), 2001 (Synapse Information Resources, Inc., Endicott, N.Y., USA); Remington's Pharmaceutical Sciences, 20th Edition, 2000, pub. Lippincott, Williams & Wilkins; and Handbook of Pharmaceutical Excipients, 2nd edition, 1994. By way of example, and the compositions are preferably administered to patients in dosages of between about 0.01 and 100 mg of active compound per kg of body weight, and more preferably between about 0.5 and 10 mg/kg of body weight.

The following is presented by way of example and is not to be construed as a limitation to the scope of the claims.

EXAMPLES

Example 1—Synthesis of Nanoparticles

Gold nanoparticles having a corona of carbohydrate ligands or glutathione ligands were synthesised essentially as described previously (WO 2011/154711; and Lund et al., 2011, Biomaterials Vol. 32 pp. 9776-9784, the entire contents of which are expressly incorporated herein by reference).

AL/α-Gal NPs

Preparation of 2-thio-ethyl-α-D-galactoside (α-galactose C2SH)

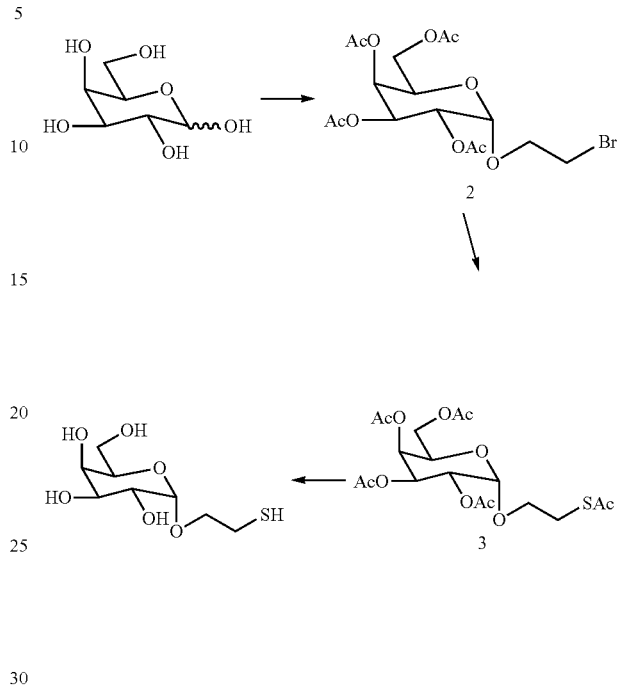

To a suspension of galactose (3 g, 16.65 mmol) in 2-bromoethanol (30 ml), acid resin Amberlite 120-H is added to reach pH 2. The reaction is stirred for 16 hours at 50-60° C. The reaction mixture is filtered and washed with MeOH. Triethylamine is added to reach pH 8. The crude of the reaction is concentrated and co evaporated 3 times with toluene. The reaction mixture is dissolved pyridine (75 mL) and Ac2O (35 mL) and a catalytic amount of DMAP are added at 0° C. and stirred for 3 h at rt. The mixture is diluted with AcOEt and washed with $1.H_2O$; 2.HCl (10%) 3. $NaHCO_3$ dis $4.H_2O$. The organic layer is collected and dried over anhydrous $Na_2SO_4$. TLC (Hexane: AcOEt 3:1, 2 elutions) shows a major product (desired) and a lower Rf minority. The product is purified by flash chromatography using the mixture hexane: ethyl acetate 6:1 as eluent and the 2-bromoethyl-alpha-galactoside (2) is obtained.

The product of the previous reaction, 2 is dissolved in 27 ml of 2-butanone. To this solution, a catalytic amount of tetrabutylammonium iodide and 4 equivalents of potassium thioacetate are added. The resulting suspension is stirred for 2 hours at room temperature. Throughout this period the reaction is tested by TLC (hexane-AcOEt 2:1, 2 elutions) for the disappearance of the starting material. The mixture is diluted with 20 ml of AcOEt and washed with a saturated NaCl solution. The organic phase is dried, filtered and evaporated under vacuum. The product is purified in hexane/AcOEt 2:1→1:1 to obtain the acetylthio-alpha-galactoside 3.

The new product of the reaction, 3 is dissolved in a mixture dichloromethane-methanol 2:1. To this mixture a solution of 1N sodium methoxide (1 equivalent) is added and stirred for 1 hour at room temperature. Amberlite IR-120H resin is added to achieve pH 5-6. The resulting mixture is then filtered and concentrated to dryness to obtain the final product (α-galactose C2SH).

Preparation of Amino-Thiol Linker.

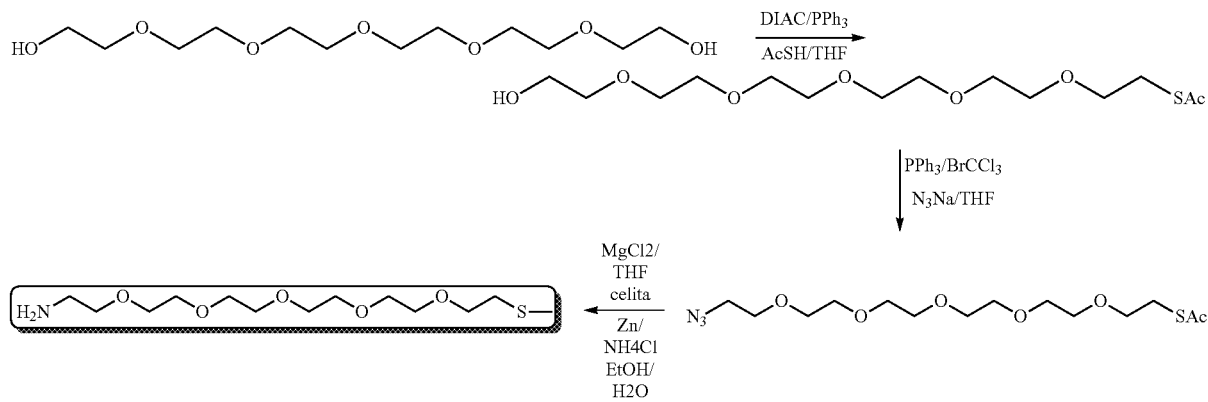

To a solution of PPh$_3$ (3 g, 11.4 mmol) in 20 ml dry THF, DIAC (2.3 g, 11.4 mmol) is added. The mixture is allowed to stir at 0° C. 15 min until the appearance of a white product. To this mixture a solution of hexaethyleneglycol (1.45 mL, 5.7 mmol) and HSAc (610 µl, 8.55 mmol) in dry THF (20 mL) is added dropwise (addition funnel). After 15 min the products begin to appear on TLC at Rf 0.2. The solution is concentrated in an evaporator. The crude of the reaction is dissolved in 50 ml of dichloromethane and washed with a solution of K$_2$CO$_3$ 10%. The organic phase is dried over anhydrous Na$_2$SO$_4$, filtered and concentrated under vacuum. Flash chromatography of the crude using AcOEt: Hexane 1:1, AcOEt and finally DCM:MeOH 4:1 as eluent gave the acetyl-thio-hexaethyleneglycol derivative.

The reaction product is dissolved in 5 ml of DMF and PPh$_3$ (2.25 g, 8.55 mmol), NaN$_3$ (0.741 g, 11.4 mmol) and BrCl$_3$C (0,845 ml, 8.55 mmol) are added and the solution subsequently stirred for 40 min at room temperature. The resulting product has a higher Rf than the starting product when performing TLC (DCM:MeOH 25:1). The reaction mixture is diluted with 100 ml of diethylether and washed three times with H$_2$O. The organic phase is dried over anhydrous Na$_2$SO$_4$, filtered and evaporated under vacuum. The product is purified by flash chromatography using the mixture of eluents DMC/MeOH 200:1 and DCM/MeOH 40:1 to obtain the azido-acetylthio-hexaethyleneglycol derivative.

To remove the triphenyl phosphine oxide, the reaction product is dissolved in 10 ml of THF and 0.5 g of MgCl$_2$ is added to this solution. The reaction is stirred for 2 h at 80° C. until a white precipitate appears and then is filtered through celite.

The product is dissolved in a mixture of ethanol:H$_2$O 3:1 and added Zn dust (0.45 g, 6.84 mmol) and NH$_4$Cl (0.6 g, 11.4 mmol). The reaction was stirred at reflux for 1 h until the presence of starting material is no longer detectable by TLC (DCM/MeOH 25:1). The reaction is filtered through celite and the solvent is evaporated. The crude de reaction is diluted with AcOEt and extract with 5 ml H$_2$O. The aqueous phase is evaporated to dryness to obtain the amino-thiol-hexaethylenglycol product.

Alpha-galactose C2 derivative 3 and hexaethyleneglycol amine linker 6 were taken from Midatech Biogune stock. N-(3-Dimethylaminopropyl)-N'-ethylcarbodiimide hydrochloride (EDC·HCl), HAuCl$_4$, NaBH$_4$ were purchased from Sigma-Aldrich Chemical Company. Imidazole-4-acetic acid monohydrochloride was purchased from Alfa Aesar. Company High quality MeOH and Nanopure water (18.1 mΩ) were used for all experiments and solutions.

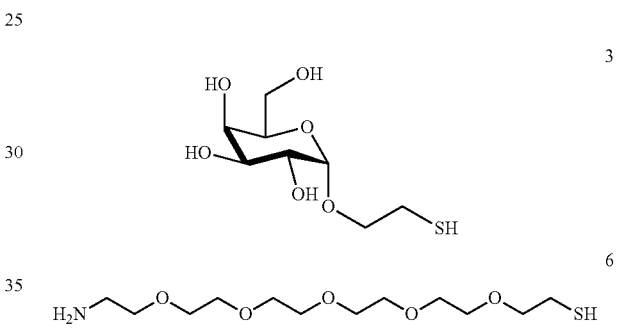

α-GalC2 (Alpha)

2'-thioethyl-α-D-galactopyranoside (alpha)

EG6NH2

1-amino-17-mercapto-3,6,9,12,15,-pentaoxa-heptadecanol or 1-amino-6-mercapto-hexaethylenglycol (vulgar name)

Preparation of AL/α-Gal NPs: To a mix of amine-mercapto hexaethylenglycol linker 6 and alpha-galactose ligand 3 in a ratio 1:1 (0.58 mmol, 3 eq.) in MeOH (49 mL) was added an aqueous solution of gold salt (7.86 mL, 0.19 mmol, 0.025M). The reaction was stirred for 30 seconds and then, an aqueous solution of NaBH$_4$ (1N) was added in several portions (4.32 mL, 4.32 mmol). The reaction was shaken for 100 minutes at 900 rpm. After this time, the suspension was centrifuged 1 minute at 14000 rpm. The supernatant is removed and the precipitated was dissolved in 2 mL of water. Then, 2 mL of the suspension were introduced in two filters (AMICON, 10 KDa, 4 mL) and were centrifuged 5 minutes at 4500 g. The residue in the filter was washed twice more with water. The final residue was dissolved in 80 mL of water.

For the preparation of gold NPs manufacture was under laminar flow cabinet. All glass and plastic material (such as eppendorfs, vials and bottles) and solvent (water, HAc) were first sterilized in an autoclave. All other disposables (such as tips and filters) came pre-sterilized.

Example 2—Bioactivity of Nanoparticles

Cell Killing

HSC-3, HaCaT, and HeLa cell lines are maintained in low glucose DMEM with 10% foetal calf serum.

For clonogenic assay, cells are seeded at a density of either 500 cells/well in 24-well plastic culture plates or at 1000 cells per well in 6-well culture plates. After allowing 24 hr for cells to attach, nanoparticles are added at the required concentration for 3 hr, then washed off and replaced with fresh medium. Cells are then maintained for 7 days to grow as individual colonies. Colonies are then stained with 0.5% w/v methylene blue in 50% ethanol. The number of colonies (>50 cells) are counted per condition and photographed under identical lighting.

For radiotherapy, the protocol is as above using 24-well plates. Cells are loaded for 3 hr with nanoparticles and then irradiated with 4Gy of 150 keV x-rays. Approximately 1 hour later the cells are washed and replaced with fresh medium and maintained for 7 days.

Figure 1:
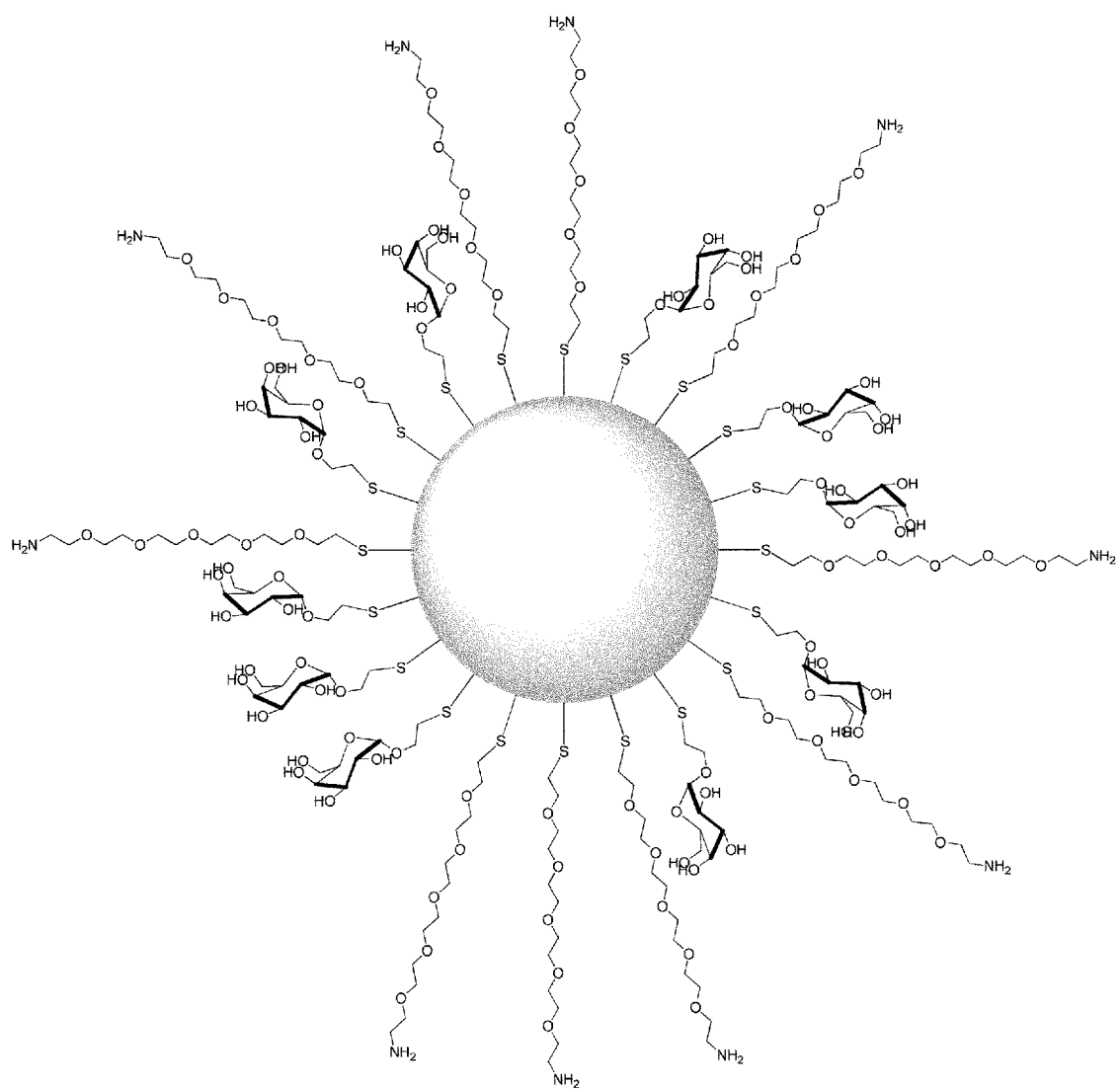
FIG. 1 shows a schematic representation of a nanoparticle having a plurality of ligands in the ratio of 1:1 of alpha-galactose:PEGamine and a gold core.
Figure 2:
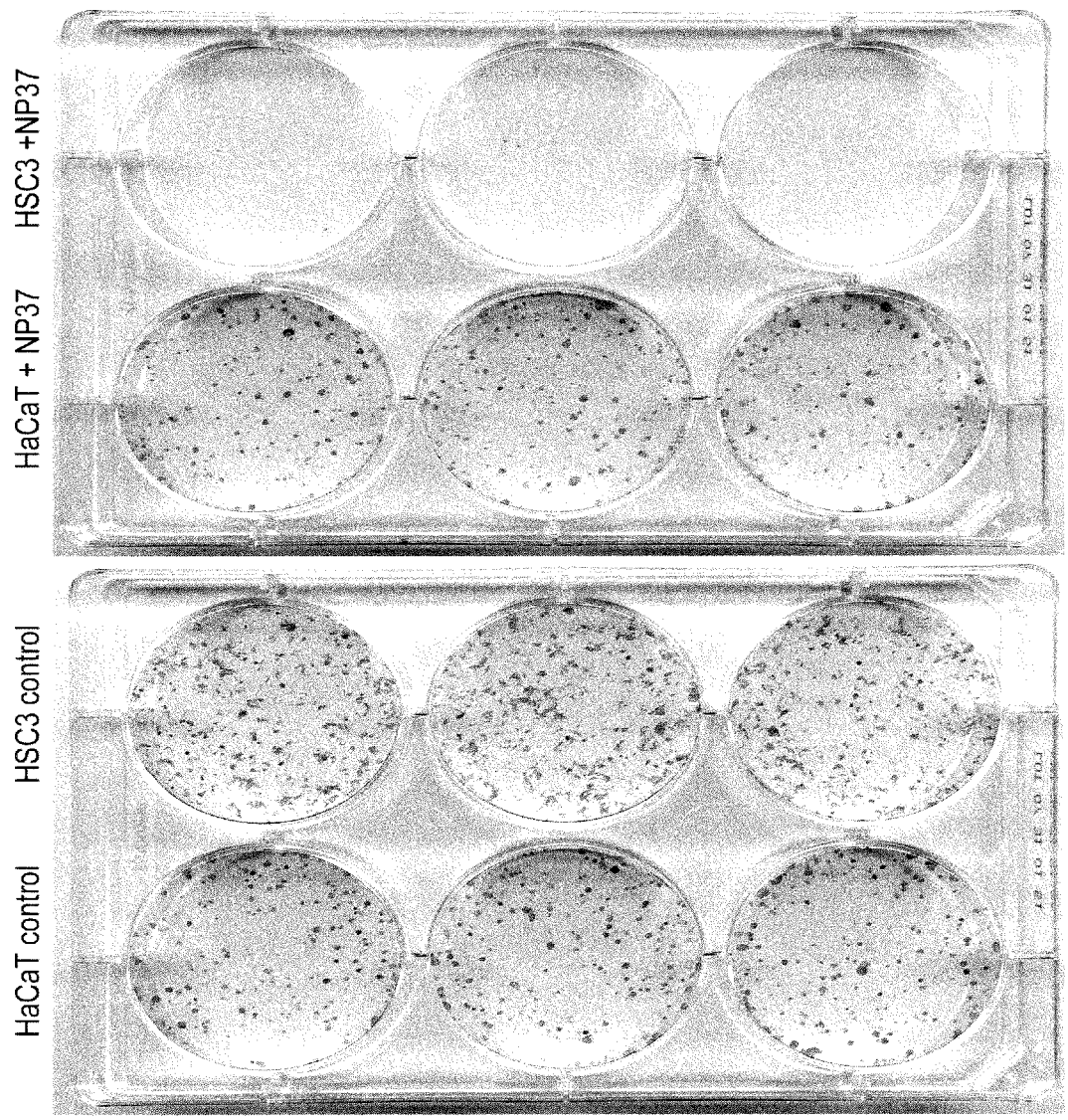
FIG. 2 shows clonogenic assay triplicate results in the form of a photograph of two six-well plates, in which: the upper row of the upper plate has three wells with HSC-3 cells+NP37 nanoparticles (50:50 alpha-galactose-C2:PEGamine-GNP); the lower row of the upper plate has HaCaT cells+NP37 nanoparticles; the upper row of the lower plate has HSC3 cells without nanoparticles (control); and the lower row of the lower plate has HaCaT cells without nanoparticles (control). The plates were seeded at 1000 cells/well for 24 hours, then exposed to NP37 nanoparticles (15 µg/ml) or no nanoparticles for 3 hours, washed out, then cultured in normal medium for 7 days. The results show that the oral SCC tumour cell line, HSC3, when treated with NP37 nanoparticles exhibited near total cell death in comparison to untreated HSC3 cells and in comparison to keratinocyte, HaCaT, cells treated with NP37 nanoparticles or untreated.

As shown in FIG. 2, clonogenic assay results show that the oral SCC tumour cell line, HSC-3, when treated with NP37 nanoparticles (50:50 alpha-galactose-C2:PEGamine-GNP) exhibited near total cell death in comparison to untreated HSC-3 cells and in comparison to keratinocyte, HaCaT, cells treated with NP37 nanoparticles or untreated.

The results shown in FIG. 3 indicate cell killing for HSC-3 cells by all three nanoparticle types, MP253 (60:40 alpha-galactose-C2:PEGamine-GNP), NP37 (50:50 alpha-galactose-C2:PEGamine-GNP), and MP254 (40:60 alpha-galactose-C2:PEGamine-GNP) in comparison to HaCaT cells. The order of potency (highest to lowest) was MP253>MP254>NP37.

A range of nanoparticle corona types were investigated for cancer cell killing activity. FIG. 4 shows clonogenic assay results of various nanoparticles to HSC-3 cells and HaCaT cells. The nanoparticle treatments were: MP184 (50:50 alpha-galactose-C2:PEGamine-GNP), MP185 (50:50 beta-glucose-C2:PEGamine-GNP), MP186 (50:50 N-acetyl-glucosamine-C2:PEGamine-GNP), MP187 (100% alpha-galactose-C2-GNP), MP188 (100% PEGamine-GNP) and untreated control "zero". The results show clear cell killing of HSC-3 cells in comparison to HaCaT cells by MP184, MP185, MP186 and MP188 at the concentration tested (15 μg/ml for 3 hours).

As shown in FIG. 5, NP37 nanoparticles killed HSC-3, HeLa and (at higher concentrations) HaCaT cells in a dose-dependent manner. The $LD_{50}$ values for NP37 nanoparticles against the three cell types are shown in Table 1. The sensitivity of the tumour cell lines HeLa (cervical) and HSC-3 (oral SCC) relative to HaCaT (keratinocytes) is indicative of therapeutic benefit in the treatment of cancer.

TABLE 1

$LD_{50}$ for NP37 in 3 cell types

| Cell type | LD 50 μg/ml |
|---|---|
| HeLa | 2 |
| HSC | 11 |
| HaCaT | 38 |

Potentiation of nanoparticle-induced HSC-3 cell killing was observed following irradiation with 4Gy 150 keV x-rays.

Mechanism of Cell Killing

The potential role for reactive oxygen species (ROS) in the nanoparticle-mediated cell death was investigated. HSC-3 and HaCaT cells were treated with 15 μg/ml NP37 nanoparticles for 3.5 hours. As shown in Table 2, the ROS-sensitive probe, DCFHDA, shows selectively higher fluorescence signal in the HSC-3 cells when NP37 nanoparticles are present. Results also indicate that nanoparticles that exhibit cell toxicity to cancer cells also cause a rise in intracellular calcium within seconds of addition. Without wishing to be bound by any particular theory, the inventors believe the calcium signalling may play a role in the mechanism of cell killing.

TABLE 2

NP37 increases reactive oxygen species (ROS) in cells

|  | HSC | HaCaT | HSC % max | HaCaT % max |
|---|---|---|---|---|
| DCFHDA only | 31.1 | 6 | 67.7 | 61.8 |
| NP37 + DCFHDA | 42 | 7 | 91.5 | 72.1 |
| DCF-ox (max) | 45.9 | 9.7 | 100 | 100 |

As shown in FIG. 8, the antioxidants sodium pyruvate and ascorbic acid are able to prevent NP37-mediated HSC-3 cell death at concentrations in the range tested. HSC-3 cells were treated with NP37 nanoparticles (30 μg/ml for 3 hours) in the presence or absence of either sodium pyruvate (Pyr) of ascorbic acid (AA) as antioxidants. The Pyr concentrations tested were: zero, 0.1 mM, 1 mM, 2 mM and 5 mM. The AA concentrations tested were: zero, 0.05 mM, 0.1 mM, 0.5 mM and 1 mM.

Cell Uptake of Nanoparticles

As shown in FIG. 6, NP37 nanoparticles exhibit rapid uptake into HSC-3 cells and HaCaT cells, with accumulation of the nanoparticles adjacent to the cell nucleus, possibly within the Golgi.

The results shown in FIG. 7 indicate greater cell uptake by HSC-3 and HaCaT cells of the nanoparticles MP184-186, with lower uptake of MP187 and MP188. The location of the majority of the staining was again found to be juxtanuclear. The nanoparticles treatments (all 15 μg/ml) were: MP184 (50:50 alpha-galactose-C2:PEGamine-GNP), MP185 (50:50 beta-glucose-C2:PEGamine-GNP), MP186 (50:50 N-acetyl-glucosamine-C2:PEGamine-GNP), MP187 (100% alpha-galactose-C2-GNP), MP188 (100% PEGamine-GNP), and zero (untreated control).

Nanoparticle penetration of skin samples was also investigated. FIG. 9 shows NP37 nanoparticle murine skin penetration following 200 μg/ml topical application of nanoparticles for 4 hours. FIG. 10 shows NP37 nanoparticle skin penetration following 200 μg/ml topical application of nanoparticles for 4 hours. Shown are: untreated control, skin treated with 200 μg/ml NP37+penetration enhancer (60 mg N-lauroylsarcosine and 40 mg sorbitan monolaurate (Span® 20) per 10 ml of phosphate buffer:ethanol (1:1)) for 4 hours, and skin treated with 200 μg/ml NP37 for 4 hours. The results indicate that NP37 nanoparticles are rapidly absorbed into murine skin.

Example 3—Further Bioactivity Experiments

Further toxicity studies were performed using the same methodology as described above in Example 2. The results are shown in FIGS. 11 and 12.

FIG. 11 shows dose-dependent toxicity (% control surviving) of various ratios of sugar:PEGamine nanoparticles against HSC-3 Oral SCC cells (left-hand panel) and HaCaT control keratinocytes. The $IC_{50}$ of the 50:50 alpha-galactose:PEGamine nanoparticles was found to be 0.96 µg/ml (approximately 50 nM), which is much lower than the $IC_{50}$ measured for the same nanoparticles against the HaCaT cells>10000 µg/ml, indicating selective anti-cancer toxicity. The 50:50 ratio alpha-galactose:PEGamine AuNPs were found to exhibit the greatest anti-cancer toxicity, followed by the 60:40 ratio alpha-galactose:PEGamine AuNPs as the next most potent.

FIG. 12 shows the results of studies investigating the ability of the nanoparticles to potentiate radiation-induced cell killing, i.e. a chemoradiotherapeutic effect. The FIG. 12 graphs show toxicity (surviving fraction; y-axis) plotted against radiation dose (Gray; x-axis) of HSC-3 cells (left-hand panel) and HaCaT cells (right-hand panel). The nanoparticle-treated HSC-3 cells exhibited enhancement of radiation-induced cell killing (approximately 1.4× for 0.3 µg/ml AuNPs; 2.8× for 0.6 µg/ml AuNPs). A much lower level of radiation potentiation was seen in the non-cancer HaCaT cells (approximately 1.0× for 0.3 µg/ml AuNPs; 1.1× for 0.6 µg/ml AuNPs).

Electron microscopy studies (TEM; not shown) demonstrate that AuNPs selectively accumulate in skin cancer cells (i.e. higher uptake by HSC cells compared with HaCaT cells). Without wishing to be bound by any particular theory, the present inventors believe that the selective toxicity of the AuNPs to the skin cancer cells may be attributable to the selective accumulation in the skin cancer cells.

These results demonstrate that the nanoparticles of the present invention are selectively toxic for cancer cells and selectively enhance radiotherapy.

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

The invention claimed is:

1. A method of treatment of a squamous cell carcinoma in a mammalian subject in need thereof, said method comprising administering to said subject a therapeutically effective amount of a nanoparticle comprising a core comprising gold; and a corona comprising a plurality of ligands covalently linked to the core, the plurality of ligands including at least a first species of ligand comprising amine-functionalized oligo (ethylene glycol) and at least a second species of ligand comprising a monosaccharide selected from the group: galactose, glucose and N-acetylglucosamine said nanoparticle killing one or more cancer cells in
   i) the absence of any cytotoxic drug or toxin bound to the nanoparticle core or corona and
   ii) in the absence of applied radiation.

2. The method according to claim 1, wherein said SCC is oral SCC or skin SCC.

3. The method according to claim 1, wherein said method further comprises administering radiotherapy to said subject.

4. The method according to claim 1, wherein said method of treating said cancer comprises administering said nanoparticle and subsequently or concurrently administering said radiotherapy to the subject.

5. The method according to claim 4, wherein said radiotherapy comprises x-ray radiation.

6. The method according to claim 1, wherein said first species of ligand comprises an amine-functionalised hexaethylene glycol.

7. The method according to claim 6, wherein said first species of ligand comprises a ligand according to formula (I):

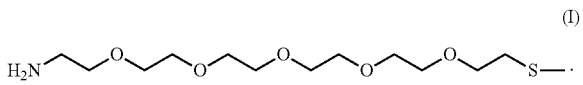

8. The method according to claim 1, wherein said second species of ligand comprises alpha-galactose covalently linked to said core via a thioethyl group.

9. The method according to claim 1, wherein said first and second species of ligands are present on the nanoparticle in a molar ratio in the range 95:5 to 5:95.

10. The method according to claim 9, wherein said first and second species of ligands are present at a ratio in the range 45:55 to 55:45.

11. The method according to claim 1, wherein the only ligands covalently linked to the core are said first species of ligand and said second species of ligand.

12. The method according to claim 9, wherein said first and second species of ligands are present at a ratio in the range 80:20 to 20:80.

13. The method according to claim 9, wherein said first and second species of ligands are present at a ratio in the range 60:40 to 40:60.

* * * * *